(12) United States Patent
Chalvignac

(10) Patent No.: US 9,089,660 B2
(45) Date of Patent: Jul. 28, 2015

(54) BREATHING ASSISTANCE APPARATUS

(71) Applicant: ResMed Paris SAS, Moissy Cramayel (FR)

(72) Inventor: Philippe Auguste Chalvignac, Moissy Cramayel (FR)

(73) Assignee: ResMed Paris (FR)

( * ) Notice: Subject to any disclaimer, the term of this patent is extended or adjusted under 35 U.S.C. 154(b) by 0 days.

(21) Appl. No.: 13/733,275

(22) Filed: Jan. 3, 2013

(65) Prior Publication Data

US 2013/0118495 A1 May 16, 2013

Related U.S. Application Data

(63) Continuation of application No. 13/024,702, filed on Feb. 10, 2011, now Pat. No. 8,353,292, which is a continuation of application No. 10/550,247, filed as application No. PCT/IB2004/001298 on Mar. 24, 2004, now Pat. No. 7,905,231.

(60) Provisional application No. 60/495,923, filed on Aug. 18, 2003.

(30) Foreign Application Priority Data

Mar. 24, 2003 (FR) ...................................... 03 03538

(51) Int. Cl.
*A62B 9/02* (2006.01)
*A61M 16/00* (2006.01)
*A61M 16/20* (2006.01)
*A61M 16/06* (2006.01)
*A62B 9/00* (2006.01)

(52) U.S. Cl.
CPC ........... *A61M 16/0057* (2013.01); *A61M 16/00* (2013.01); *A61M 16/06* (2013.01); *A61M 16/20* (2013.01); *A61M 16/206* (2014.02); *A61M 16/0066* (2013.01); *A61M 2016/0021* (2013.01); *A61M 2016/0039* (2013.01); *A61M 2016/0042* (2013.01); *A62B 9/006* (2013.01)

(58) Field of Classification Search
USPC .............. 128/204.18, 204.21–204.23, 205.24
See application file for complete search history.

(56) References Cited

U.S. PATENT DOCUMENTS 2,219,324 A * 10/1940 Lee ................................ 251/123
3,961,627 A 6/1976 Ernst et al.
4,237,925 A * 12/1980 Urushida ....................... 137/552

(Continued)

FOREIGN PATENT DOCUMENTS

FR 2812203 A1 2/2002

*Primary Examiner* — Kristen Matter
(74) *Attorney, Agent, or Firm* — Lerner, David, Littenberg, Krumholz & Mentlik, LLP

(57) ABSTRACT

A breathing assistance apparatus capable of operating in alternating inhalation and expiratory phases includes a pressurized respiratory gas source, an inhalation duct to supply gas from the pressurized respiratory gas source to a patient, and an expiratory duct for expiratory gas of the patient. The apparatus further includes a set of flow rate sensors positioned to sense a first flow rate of the expiratory duct and a second flow rate of the inhalation duct, and a controller, including a processor, configured to control the gas source. The inhalation duct includes an inhalation valve, the inhalation valve configured to provide proportional operation and the inhalation valve is selectively controlled by the controller to move to a specific position to allow a desired level of flow through the inhalation valve to the patient.

27 Claims, 3 Drawing Sheets

(56) References Cited

U.S. PATENT DOCUMENTS

| | | |
|---|---|---|
| 5,307,795 A | 5/1994 | Whitwam et al. |
| 5,308,040 A | 5/1994 | Torres |
| 5,417,083 A | 5/1995 | Eber |
| 5,503,146 A | 4/1996 | Froehlich et al. |
| 5,540,220 A | 7/1996 | Gropper et al. |
| 5,735,267 A | 4/1998 | Tobia |
| 5,813,410 A | 9/1998 | Levin |
| 5,937,853 A | 8/1999 | Strom |
| 6,095,139 A | 8/2000 | Psaros |
| 6,102,038 A | 8/2000 | DeVries |
| 6,279,574 B1 * | 8/2001 | Richardson et al. ...... 128/204.18 |
| 6,439,229 B1 | 8/2002 | Du et al. |
| 6,470,857 B2 | 10/2002 | Takahashi et al. |
| 6,622,726 B1 | 9/2003 | Du |
| 6,626,175 B2 | 9/2003 | Jafari et al. |
| 6,759,934 B2 * | 7/2004 | Bircann et al. ................ 335/255 |
| 7,905,231 B2 | 3/2011 | Chalvignac |
| 2002/0014239 A1 | 2/2002 | Chalvignac |
| 2002/0053345 A1 * | 5/2002 | Jafari et al. .............. 128/204.23 |

\* cited by examiner

BREATHING ASSISTANCE APPARATUS

CROSS-REFERENCE TO RELATED APPLICATIONS

This application is a continuation of U.S. application Ser. No. 13/024,702, filed Feb. 10, 2011, now U.S. Pat. No. 8,353,292, which is a continuation of U.S. application Ser. No. 10/550,247, filed on Aug. 15, 2006, now U.S. Pat. No. 7,905,231, which is a national phase entry under 35 U.S.C. §371 of International Application No. PCT/IB2004/001298, filed on Mar. 24, 2004, which claims the benefit of French Application No. 0303538, filed on Mar. 24, 2003, and of U.S. Provisional Patent Application No. 60/495,923, filed on Aug. 18, 2003, the disclosure of which is hereby incorporated herein by reference.

BACKGROUND OF THE TECHNOLOGY

This invention concerns a breathing assistance apparatus capable of operating in alternating inhalation and expiratory phases and comprising:
 a pressurized respiratory gas source,
 control means capable of transmitting a reference value of a gas related parameter to the said gas source,
 an inhalation duct to supply the gas from the gas source to a patient,
 an expiratory duct for the expiratory gas of the patient,
 a valve on the inhalation duct, said valve comprising means that allow the gas to pass to make possible proportional operation, said valve being controlled by means which are distinct from the pressurized gas source,
 a valve on the expiratory gas source to help establish a PEP,
 sensors, respectively pressure and flow, on the inhalation duct.

It is pointed out that the PEP (Positive Expiratory Pressure) will be defined below.

Apparatus of the type mentioned above are already known.

For example, a description of such an apparatus can be found in the document FR 2 812 203 (see FIG. 15 of this document for example).

FIG. 1 shows a diagrammatic representation of a known apparatus 10.

The apparatus 10 comprises a source 100 of pressurized respiratory gas connected to a first end of an inhalation duct 110, whose second end is in contact with a patient to supply him/her with gas from the source 100 during the inhalation phases.

This second end is shown here by a breathing mask 120. It can also be envisaged to use an apparatus of this type in "invasive" mode, the patient then is intubated with this second end of the duct.

The mask may have vents for leaks from the breathing mask.

The apparatus 10 also comprises an expiratory duct 130, whose first end is open to free air to evacuate the gases exhaled by the patient, and whose second end is connected to the patient, joining the second end of the inhalation duct.

Two sensors can be seen on the inhalation duct 110:
 a respiratory gas pressure sensor 111 in the duct,
 a flow rate sensor 112 for this same gas.
Valves are fitted in order to close the respective ducts 110 and 130 selectively.

A valve 113 is thus placed on the duct 110, and a valve 133 on the duct 130.

The valve 113 that is positioned on the inhalation duct is the type of valve whose means for allowing the gas to pass comprise at least one part permitting proportional operation.

Typically, this concerns a valve in which the gas passage means include a cock that can be moved in rotation.

The operation of such a valve capable of operating proportionally corresponds to a specific configuration (proposed in the document FR 2 812 203) that is advantageous. We will come back to this aspect.

The valve 133 that is positioned on the expiratory duct is a different type of valve.

This valve comprises an inflatable bladder type sealing element capable of blocking the duct on which the valve is positioned and is pneumatically controlled.

The valve 113 is controlled by a dedicated electric motor (not shown).

The valve 133 is pneumatically controlled.

More precisely, the valve 133 can be selectively controlled by two different pressure lines, as this valve is connected to pressure line selection means which control the valve.

These two pressure lines are:
 a line 1331 connected to the pressure source 100,
 a line 1332 connected to an auxiliary pressure source 140.

The apparatus 10 also comprises an assembly collectively designated under the reference 50, which corresponds to means for controlling the operation of the apparatus.

These control means 50 are capable of defining a reference operating value for the gas source 100, and transmitting it by means of a connection 1510.

This reference operating value is for example expressed in a number of revolutions per minute, in the case of the pressure source 100 being a turbine. It may also be a different type of reference value, for example a pressure output reference value from the pressurized gas source.

The reference value is a real time reference value and is constantly adapted by the control means 50.

Such an apparatus operates according to an alternating rhythm of:
 inhalation phases when the valve 113 is in the open position and the valve 133 is in the closed position.
 expiratory phases when the valve 113 is in the closed position and the valve 133 is:
  either in the open position,
  or in the closed position so as to establish a positive counter pressure in the expiratory duct (PEP), which is designed to balance the residual excess pressure in the patient's lungs when the said patient is in the expiratory phase. In this case, a specific control for sealing the valve 133 is provided.

The reference value defined by the control means 50 to be transmitted to the pressurized gas source 100 is composed according to a parameter that is representative of the operation of the apparatus. We will come back to this aspect as part of the description of the invention.

Also, according to the nature of the parameter that is representative of the operation of the apparatus that is used to define this reference value for the gas source, the apparatus may be operated in different operating modes.

In particular, this apparatus can operate in barometric or volumetric mode.

In barometric mode, the apparatus is controlled according to the pressure in the inhalation duct. In this operating mode, the objective is to provide the patient with a desired pressure during each inhalation phase (see FR 2 812 203 page 19).

In this operating mode, it is a pressure parameter that is consequently used to define the reference value for the source

100. The flow rate in the inhalation duct is a value which results from the pressure control.

In volumetric mode, the apparatus is controlled according to the flow rate in the inhalation duct. In this operating mode, the objective is to provide the patient with a desired volume of gas during each inhalation phase (see FR 2 812 203 page 18).

More precisely, in the volumetric mode, the apparatus of FR 2 812 203 is controlled as follows to provide the patient with a desired volume of gas.

The apparatus of FR 2 812 203 comprises an inhalation valve with a rotating element whose rotation is controlled so as to form in the inhalation valve a passageway section having a dimension which corresponds to the volume which is desired for the patient.

The angular position of the rotating element of the inhalation valve is thus set at a value corresponding to the volume which is to be delivered to the patient.

Once a value of the desired volume to be delivered to the patient has been selected, this rotating element is brought into an angular position which corresponds to said value.

Furthermore, in the volumetric mode of the apparatus of FR 2 812 203 the pressure difference between the upstream and downstream parts of the inhalation valve is kept constant through the control of the pressure at the outlet of the gas source of the apparatus.

Thus, in the volumetric mode the apparatus of FR 2 812 203 undergoes two controls:
   (a) control of the volume of gas delivered to the patient. This is achieved through the control of the angular position of the rotating element of the inhalation valve. For this purpose the angular position of said rotating element is brought to a position which defines in the inhalation valve a passageway which corresponds to the desired gas volume,
   (b) control of the difference between the upstream and downstream parts of the inhalation valve. For this purpose the turbine is controlled by a control circuit of the apparatus. This pressure difference is controlled so as to keep a constant value, whatever the desired volume (or flow) for the patient.

Keeping the pressure difference between the upstream and the downstream parts of the inhalation valve at a constant level (e.g., 10 mbars) allows having an inhalation valve which operates in a linear manner, e.g. the dimension of the passageway defined by the aperture of the rotating element shall be proportional to the flow going through the valve.

Coming back to the general features of the apparatus of FR 2 0812 203, the means for controlling the apparatus are provided to adapt simultaneously:
   the operating mode (barometric or volumetric). To this end, it is possible to provide for manual selection of the operating mode desired, by an operator commanding an interface dedicated to this task (the keyboard of the apparatus for example).
   and the value of the parameter that is representative of the operation of the apparatus that is used to define the reference value for the gas source, depending on:
      the operating mode used (barometric or volumetric, which determines in particular the nature of the parameter to be used) and,
      the phase in which the apparatus is situated (inhalation or expiratory phase).

It is pointed out that if a PEP is to be used, the pneumatic pressure used to inflate the expiratory valve 133 bladder (control pressure) must be controlled with precision.

In fact, when a PEP is to be established in the mask 120 (or more generally at the patient, this text considering as equal the configuration with the mask and the invasive configuration, whether we are considering the presentation of the state of the technique or in that of the invention), the valve 133 must not be sealed by an excessive control pressure, but only by a counter pressure suitable for creating a PEP desired at the patient's level.

This is the reason why two control lines are provided for this valve 133:
   the line 1331 allows the valve 133 to be sealed without having to worry about any balancing with a counter pressure in the ducts—especially during inhalation phases,
   the line 1332, connected to the compressor, 140, permits a calibrated control pressure to be transmitted to the valve 133 in order to establish a desired PEP during the patient's exhalation during the expiratory phases.

It is pointed out that the valve 133 is connected to selection means (not shown) to select the line 1331 or the line 1332.

The known apparatus of FIG. 1 is advantageous.

In particular, the inhalation valve of such a apparatus permits precise control of the respiratory gas in the inhalation duct—including for managing different operating modes.

It can however be envisaged to improve such an apparatus event 25 further.

Firstly, it would be advantageous to have means for controlling the apparatus that allow its operation to be controlled precisely, in its various operating modes.

In particular, when operating in volumetric mode, it is possible that very precise control of the flow rate value in the duct 110 is difficult.

This is especially the case when the pressure source is a turbine.

In this case indeed, the variations in load of the turbine are likely in certain conditions to disrupt the precision of the control of the respiratory gas flow in the duct 110.

This aspect is further strengthened in the case where the inhalation gas flow rate is to be controlled over wide ranges of possible values—for example from 1 to 180 liters/minute.

Such a range of flow rates may be desired, to allow pathologies and illnesses of different types to be treated.

Secondly, it can be difficult to minimize the base flow rate.

In general, it is preferred to minimize this base flow rate during the expiratory phases, in particular to avoid wasting secondary gases such as oxygen which can be mixed in the gas issued from the source 100.

It is therefore desired that a base flow rate whose value just corresponds to the leaks of the apparatus (for example leaks in the mask 120).

This aspect in a way brings us back to the precise control of a flow rate, especially for very low reference values.

BRIEF SUMMARY OF THE TECHNOLOGY

One purpose of the invention is to improve the above-mentioned aspects.

Another purpose of the invention is to permit among others to manage (setting the reference value, regulation, etc.) accurately the connection flow rate, and the PEP, separately.

Yet another purpose of the invention is to allow close control of the leaks of the apparatus to be made, even in the case of the end of the apparatus connected to the patient is a mask. Another purpose is to permit new inhalation phases to be triggered automatically based on this control.

Yet another purpose of the invention is to provide efficient and reliable means for controlling the operation of the apparatus in volumetric modes. In particular, it would be advantageous to finely control small target values of the volume of gas to be delivered to a patient.

Finally, another purpose of the invention is to allow the benefits of a configuration in which the inhalation valve is capable of operating proportionally to be maximized.

In order to achieve these objectives, the invention proposes a breathing assistance apparatus capable of operating in alternating inhalation and expiratory phases and comprising:

a pressurized respiratory gas source, controls capable of transmitting a reference value of a parameter related to the gas to the said gas source, an inhalation duct to feed the gas from the gas source to a patient, an expiratory duct for the expiratory gas of the patient, a valve on the inhalation duct, the said valve comprising means that allow the gas to pass to make possible proportional operation, the said valve being controlled by means which are distinct from the pressurized gas source, a valve on the expiratory gas source to help establish a PEP, sensors, respectively pressure and flow, on the inhalation duct, the apparatus being characterized in that:

the said control means comprise selection means capable of selecting a pressure parameter or a flow rate parameter to define the said reference value for the gas source the said selection means are controlled by an automatic control unit, the said control unit being:

connected to the pressure and flow rate sensors situated on the inhalation duct to form a direct closed regulation circuit for selecting a reference value parameter, associated to a program allowing the selection to be made in real time from a pressure or flow rate signal.

so that the association of a direct closed regulation loop for the selection of a reference value parameter with a valve permitting proportional operation, allows real time control of barometric and volumetric operating modes of the apparatus, between the inhalation and expiratory phases and during these phases.

Preferred, but non limiting aspects of this apparatus are the following:

during the expiratory phases of the apparatus, the inhalation valve is capable of generating on its own a leak rate to compensate the leaks, so that no leak connection is associated to the inhalation valve, the pressurized gas source is a centrifugal fan type turbine with an axial air intake and peripheral output, with an inertia value less than around 150 gcm$^2$, a second flow sensor is associated to the expiratory duct, and the said flow rate sensors of the inhalation and expiratory ducts are connected to comparison means to compare the respective flow rates in the inhalation and expiratory ducts, the said comparison means are associated to processing means capable of filtering the difference between the said respective flow rates in real time, that the said processing means are connected to the said control unit, and these processing means are connected to a memory and a processor programmed to trigger a new inhalation phase when the said filtered difference is higher than a determined threshold, the inhalation valve comprises:

a valve body comprising an orifice connected to the inhalation duct, and, a moving element capable of blocking the said orifice in a closed position, and at least partially free this orifice in the open position, the said moving element featuring a recess that can be aligned with the said orifice of the valve body to allow the gas from the gas source to pass through to the inhalation duct, the said recess comprising:

a first part, whose geometry corresponds to a proportional operation of the inhalation valve when the said first part is aligned with the said orifice, a second part, whose geometry corresponds to an all or nothing operation of the inhalation valve when the said second part is aligned with the said orifice, the said recess is shaped so that when the said moving element moves to move the inhalation valve from its closed position to its open position, the said first part is first of all aligned with the recess, then the said second part is then aligned with the said recess, if this movement continues, the recess comprises:

said first part of the recess is more or less triangular, the said second part of the recess is more or less rectangular, and a base of the triangle of the first part of the recess is parallel with one side of the rectangle of the second part of the recess, to control the PEP, the expiratory valve is controlled by a micro-turbine, the micro-turbine is directly connected to the expiratory valve, no intermediate element is positioned between the micro-turbine and the expiratory valve.

The invention also concerns an operating control process of an apparatus as mentioned above, characterized in that to establish a PEP during the expiratory phases, the closure of the expiratory valve is controlled by a micro-turbine.

In such process, when the apparatus operates, the micro-turbine can operate constantly and the valve can be controlled by the selective connection of a pneumatic control line of the said valve with the micro-turbine.

Finally, the invention also concerns a process for operating an apparatus as mentioned above in a volumetric mode, characterized in that when a volumetric mode is selected the control of the volume delivered to a patient is obtained by the control of the gas source on the basis of a measured pressure parameter on the inhalation duct.

Preferred but non limiting aspects of such process are the following:

no pressure difference between an upstream part and a downstream part of the inhalation valve is used, said control of the gas source is obtained through the control of the rotation speed of a rotor of said gas source.

BRIEF DESCRIPTION OF THE DRAWINGS

Other aspects, purposes and advantages will become clearer upon reading the following description of the invention, made with reference to the appended diagrams in which, among others, FIG. 1 which has already been commented on earlier with reference to the state of the art.

DETAILED DESCRIPTION

Figure 2:
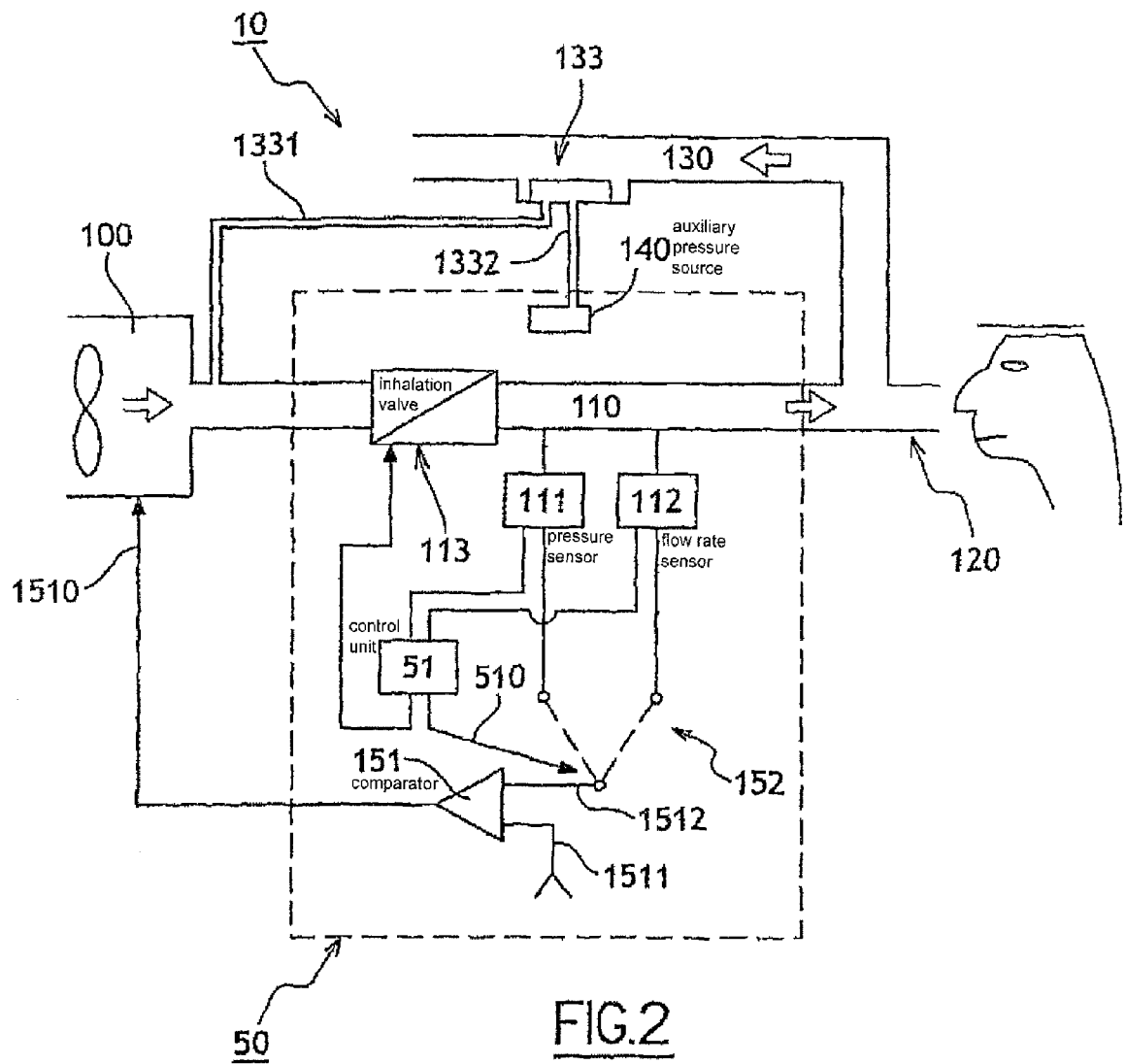
FIG. 2 is a diagrammatic representation of a first embodiment of the invention.

In reference to FIG. 2, a first embodiment of the invention has been represented.

Figure 1:
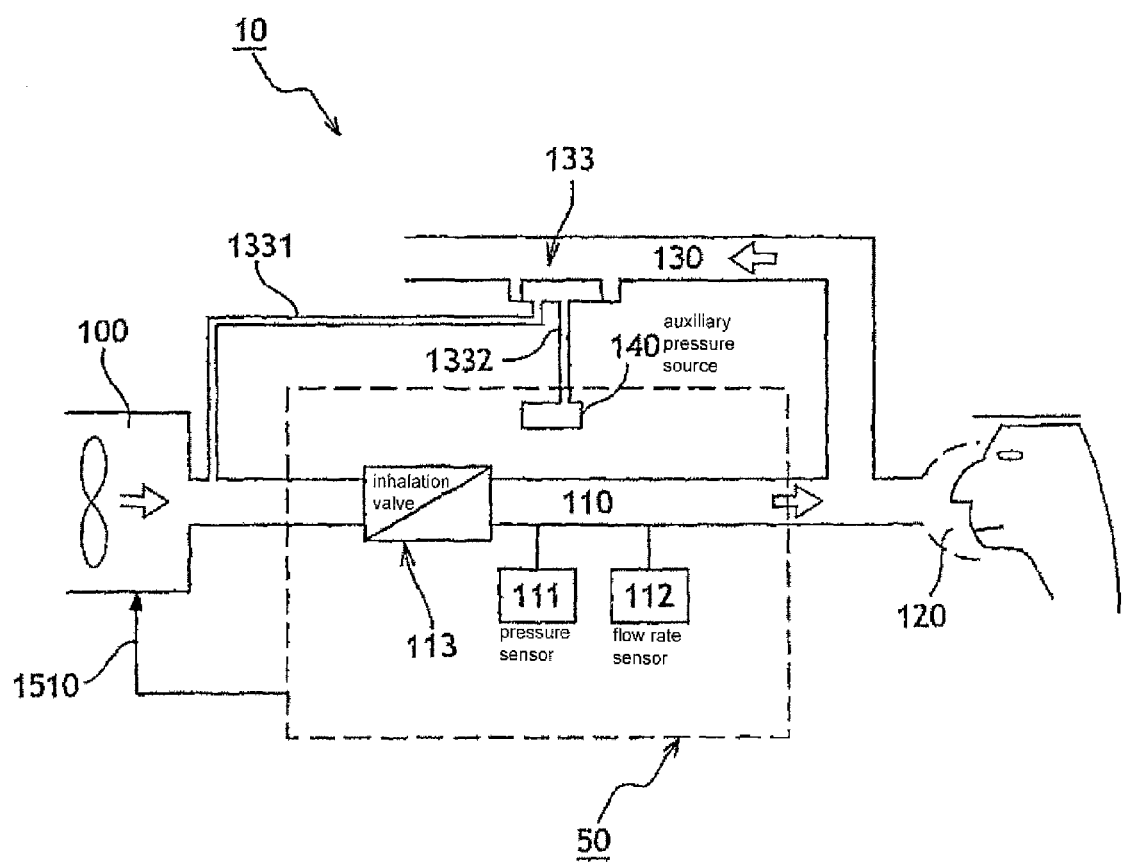
Figure 4:
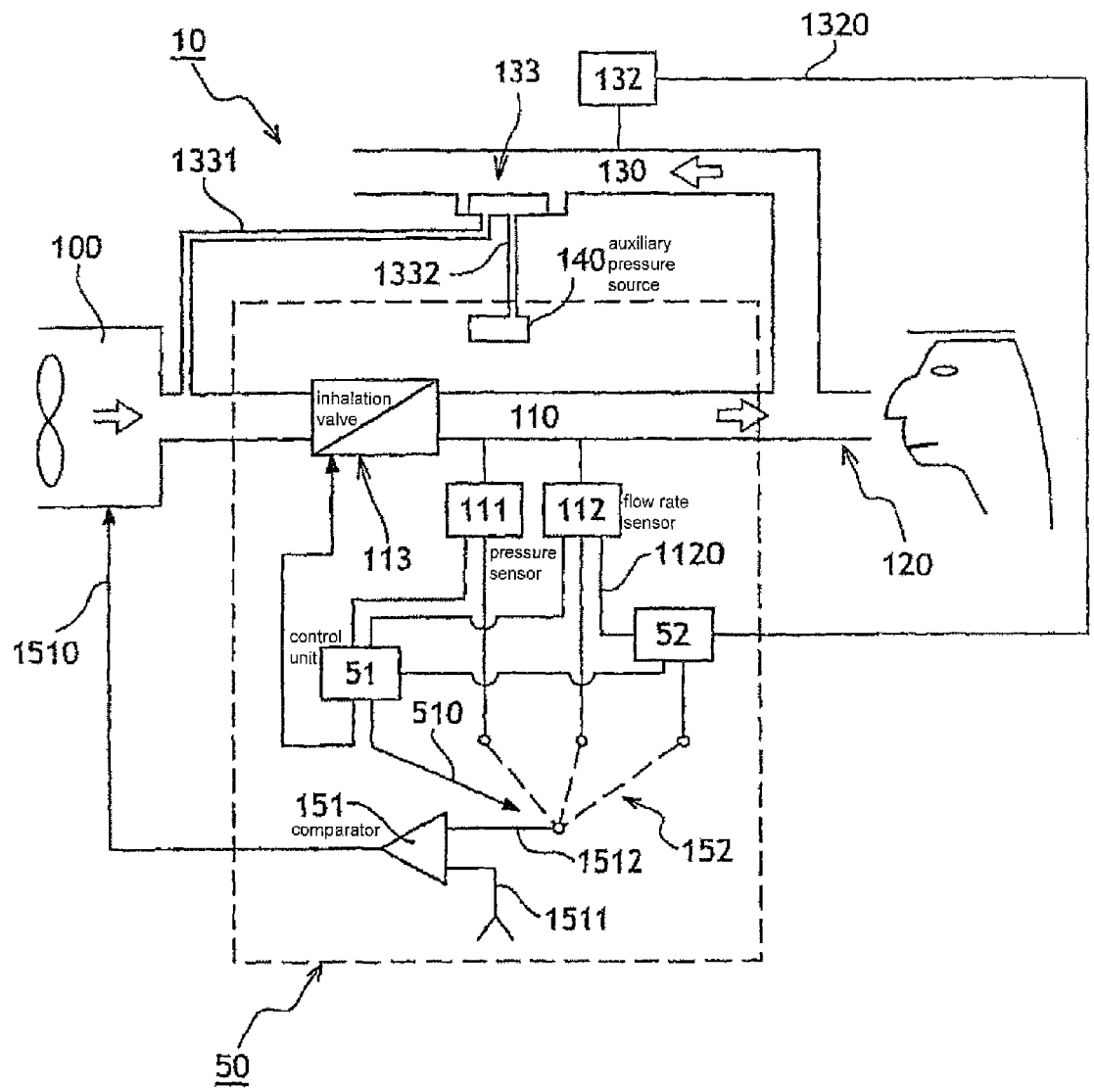
FIG. 4 is a diagrammatic representation of a second embodiment of the invention.

In this figure, as in FIG. 4, the apparatus represented comprises the elements that have already been described in reference to FIG. 1. These elements will be represented with the same references.

Consequently in this figure, we find all of the elements which make up the apparatus of FIG. 1.

In particular, we find the pressurized gas source 100.

Within the scope of the invention, this source is a centrifugal fan type turbine (which is to say that its output is on the side of the rotating element, for example via a tangential manifold pipe) with an axial air intake (which is to say that its air input is more or less aligned with the spindle of the rotating part of the turbine).

Also, this gas source has a particularly low inertia, of around 150 gcm$^2$.

We also find an inhalation valve 113 that is capable of operating proportionally.

More precisely, this valve preferably comprises a cock that can be controlled in rotation in a tubular body, so as to permit an "all or nothing" or a "proportional" operation. We will come back to this aspect.

We can also remark on this figure that the end 120 of the duct 110 is shown in the form of a mask.

In fact, the invention can be used with the end of its duct 110 corresponding to a mask (non-invasive mode) or an invasive mode (for example insertion of ducts in patient).

In the case of this end 120 being in the form of a mask, the invention allows, as we will see, the leaks associated to such a mask to be controlled precisely.

It can be seen on FIG. 2 that the apparatus control means 50 have a specific structure.

More precisely, the control means comprise:
a comparator 151, to define the operating reference value to be transmitted to the pressurized gas source via the connection 1510. This comparator has two inputs:
an input 1511 for one or more reference values. These reference values can be stored in a memory of the control means 50. One or more reference values can therefore be stored in this way, in particular for:
a pressure parameter, and;
a flow rate parameter.
an input 1512 for a representative operating value of the apparatus. This value is a pressure or flow rate value. As we will see, this value is taken from:
the pressure sensor 111 for a pressure value,
the flow rate sensor 112—or a flow rate measurement processing unit—for a flow rate value,
a switch 152 capable of selectively connecting the input 1512 of the comparator 151 with the pressure sensor 111, or the flow rate sensor 112. This switch therefore corresponds to a means of selection. It is pointed out that means are associated to the comparator 151 to provide a reference value of the same nature (pressure or flow rate) to the input 1511 of this comparator as the value transmitted to the input 1512 of the comparator, according to the position of the switch.
a control unit 51 capable of controlling the operation of the switch 152, by means of a connection 510. This control unit is also connected to:
the sensors 111 and 112, from which it receives the measurements in real time,
the motor controlling the valve 113, to control its operation. In fact, the opening of the valve cock must be directly proportional:
to the desired flow rate, in the volumetric mode,
to a desired pressure ramp, in the barometric mode.

The switch control allows the operation of the pressure source to be regulated based on the pressure measurements (barometric mode) or the flow rate measurements (volumetric mode).

Also, according to the position of the switch 152, which determines the operating mode of the apparatus (barometric or volumetric), an adapted reference value (of pressure or flow rate) is as stated provided to the reference value input 1511.

When the switch 152 connects the input 1512 to the output of the pressure sensor 111, the apparatus is set to barometric mode.

Now when the switch 152 connects the input 1512 to the output of the flow rate sensor 112, the apparatus is set to volumetric mode.

The control means 50 thus comprise a direct closed regulation circuit between the sensors 111 and 112, which characterize in real time and continuously the operation of the apparatus, and the pressurized gas source 100.

This direct closed regulation circuit permits the reference value transmitted to the source 100 to be adjusted in real time.

It also permits the operating mode to be modified in real time:
the selection of the sensor 111 using the switch corresponds to a 5 barometric mode,
the selection of the sensor 112 using the switch corresponds to a volumetric mode.

More precisely, this regulation circuit permits the nature (pressure or flow rate) of the parameter from which the operating reference value of the source 100 is defined to be modified within a phase (inhalation or expiratory).

More precisely still, the specific combination according to the invention of the following elements:
a low inertia centrifugal fan type turbine with axial intake,
an inhalation valve capable of operating proportionally,
a direct closed regulation loop using means to select the nature of the parameter (flow rate or pressure), controlled automatically and in real time by the control unit 51,
is particularly advantageous.

This combination permits in fact to control the operation of the apparatus with great precision in real time. This advantage extends to the control of wide ranges of flow rates, as mentioned in the introduction of this text.

This combination also permits the source 100 to be controlled with great precision, in particular in the perspective of the purposes and objectives of the invention previously mentioned in this text.

This configuration, which permits the operating mode to be changed in real time, based on monitoring of the operation of the apparatus and the parameters stored in a memory of the means 50 connected to the control unit, thus also offers very flexible use.

In its different variants, the apparatus according to the invention can be operated in particular in a volumetric mode.

In such case, the operation of the device is different from the operation of the device disclosed in FR 2 812 203.

Indeed, in the case of the present invention the volumetric modes are operated on the basis of a control of the gas source.

More precisely, the gas source is permanently controlled (through connection 1510) as a function of the desired gas flow (or volume) to be delivered to the patient.

More precisely even, in volumetric modes the flow is permanently measured by the flow sensor 112, and exploited by the control means 50 to control the operation of the gas source 100.

It is specified that in the volumetric modes the rotating element of the inhalation valve 113 is controlled at the beginning of each inspiratory cycle so that it takes a certain position.

Then, during the inspiratory cycle, the position of this rotating element does not change anymore.

The "certain position" mentioned above corresponds to an opening of the inhalation valve which allows a flow value through the valve substantially equal to the value desired for the patient.

But in the case of the invention, the control of the apparatus is then not performed so as to keep a pressure difference between the upstream and downstream parts of the inhalation valve (like it is the case in the apparatus of FR 2 812 203).

Instead, it is the operation of the gas source itself which is permanently controlled.

It is specified that the control of the gas source is preferably the control of the rotation speed of the rotor of the compressor of the gas source in the case of a gas source which is a turbine—or compressors, these two terms being understood as equivalent in the present text).

And in the case of the invention the flow measured in the duct 110 is exploited for controlling the gas source.

As mentioned above, the configuration presented above allows among others the operation according to different modes (and a change of the respiratory mode in real time within a given respiratory cycle).

For example, it is possible to operate the apparatus in VAPS (Volume Assured Pressure Support) mode in real time.

Such a mode uses the barometric mode and can transfer the mode to a volumetric mode in real time—including within a same inhalation or expiratory cycle.

More precisely, in this mode, an inhalation phase comprises:
- at the beginning, operation in barometric mode,
- an algorithm then monitors the volume of respiratory gas supplied to the patient on a constant basis, and extrapolates the volumes already supplied during the inhalation phase to determine if in a given pre-determined time, a pre-determined target volume will be indeed supplied to the patient during this phase.
- if the algorithm determines that this is not the case, the operation of the apparatus is forced into volumetric mode to supply the patient with a volume which permits this target to be met.

It is clear that in such a mode, the switch 152 plays an important role (in particular for the forced mode change mentioned).

Also, the specific combination mentioned above is particularly advantageous for applying this mode.

Similarly, the invention significantly facilitates the application of other modes, for example the SIMV (Synchronous Intermittent Mandatory Ventilation) mode.

It can be remarked in FIG. 2 that the auxiliary pressure source 140 which controls the pressure line 1332 of the expiratory valve is directly connected to this valve, with no intermediate elements.

This measure is made possible by the use of a micro-turbine for the auxiliary pressure source 140.

In fact, such a micro-turbine does not generate the unwanted side effects (vibrations, operating anomalies, etc.) observed with traditional auxiliary pressure sources such as compressors, on flap of which is controlled by an alternating back and forth movement.

It thus permits to dispense with the additional means (filters, etc.) that are usually positioned between the auxiliary pressure source and the expiratory valve, to protect this valve from the unwanted side effects.

The micro-turbine 140 can operate continuously, without its operation needing to be regulated.

In this case, the expiratory valve is controlled by selective connection between the control line 1332 of the expiratory valve and the micro-turbine.

This selective connection is provided by selection means (not shown) associated to the valve 135.

It is pointed out that the end 120 is fitted with a pressure sensor to monitor, during the expiratory phases, the pressure at the patient and to transmit, in real time, this pressure to the control unit 51 for control by the control unit by means of a regulation circuit (not shown) of the compressor 140.

It has already been stated that the inhalation valve 113 was capable of operating proportionally.

More precisely, in one embodiment of the invention, this valve comprises:
- a valve body comprising an orifice connected to the inhalation duct, and,
- a moving (rotating) element, such as a cock, capable of blocking the said orifice in a closed position, and at least partially free this orifice in the open position.

The said moving element features a recess that can be aligned with the said orifice of the valve body to allow the gas from the gas source to pass through to the inhalation duct, the said recess comprising:
- a first part, whose geometry corresponds to a proportional operation of the inhalation valve when the said first part is aligned with the said orifice,
- a second part, whose geometry corresponds to an all or nothing operation of the inhalation valve when the said second part is aligned with the said orifice.

The recess of the cock may be shaped so that when the said cock 5 moves to move the inhalation valve from its closed position to its open position, the said first part is first of all aligned with the recess, then the said second part is then aligned with the said recess, if this movement continues.

In this way, the command to open the inhalation valve causes firstly a progressive opening (corresponding to a proportional operation of the valve), then an extension of the opening of the valve to an all or nothing mode.

Figure 3:
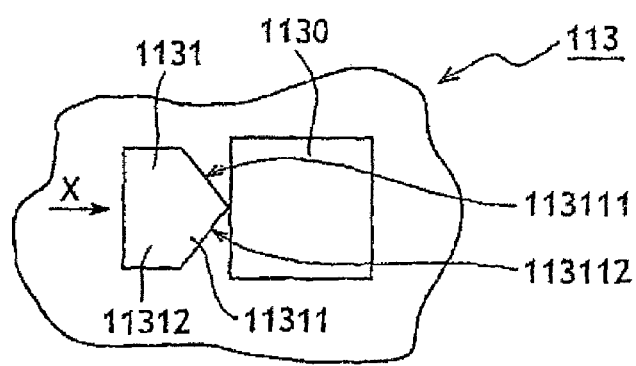
FIG. 3 is a diagrammatic representation of part of an inhalation valve 15 used in an apparatus according to the invention.

FIG. 3 shows diagrammatically in a developed view an orifice 1130 in the body of the valve and a recess 1131 of a cock.

The orifice 1130 is rectangular.

The recess 1131 has a contour formed by a first part 11311 that is more or less triangular, and a second part 11312 that is more or less rectangular.

A base of the triangle of the first part of the recess is parallel with one side of the rectangle of the second part of the recess.

This configuration permits both rapid opening of the valve 113 and very good control.

In particular, in volumetric modes fine control can be achieved for small desired values of flow, and quick operation can be achieved for higher desired values of flow.

Indeed, when a small volume is desired for the patient in a volumetric mode, the cock of the valve is controlled so as to make a small angular move between the closed position of the valve and a target angular position.

This target angular position shall typically define a passageway for the flow of gas with the "proportional" part 11311 of opening 1131.

This allows a fine definition of the volume which will flow through the passageway of the valve.

This allows control of flow values as small as 4 liters/minute in volumetric modes, while the prior art apparatuses generally only allowed control of flow values larger than about 20 liters/minute.

For larger desired values of the flow, the angular position can possibly define a passageway for the flow of gas with the contribution of the part 11312 of opening 1131.

In this part of the aperture, the rotation of the cock allows to reach faster an angular position corresponding to the large desired value for the flow.

However, in a preferred embodiment of the invention the aperture 1311 of the cock shall be designed so that the volumetric modes shall use only the first part 13111 of this aperture.

In this preferred embodiment, the other part 13112 of the aperture shall correspond to angular positions of the cock used for barometric modes.

In these barometric modes indeed, the cock can typically be controlled so as to be wide open at the beginning of an inspiratory cycle, and a large passageway through the valve is desired to control the operation of the apparatus on the basis of a pressure parameter. This is obtained by the fact that the first part 11311 of the recess 1131 has two edges 113111 and 113112 angled with respect to the direction X that the cock moves in with respect to the valve body.

FIG. 4 represents a variant of an embodiment of the invention.

In the embodiment, another flow sensor 132 is positioned on the exhalation duct 130.

The control means 50 comprise among others comparison and processing means 52 which are connected to the flow sensors 112 (by a connection 1120) and 132 (by a connection 1320).

These means 52 are capable of monitoring and comparing the respective flow rates in the inhalation 110 and expiratory 130 ducts in real time.

These means are also associated to processing means capable of filtering the difference between the said respective flow rates in real time.

These means 52 therefore monitor in real time the difference in flow rate between the inhalation and expiratory ducts.

The said processing means are connected to the control unit 51.

They include among others a memory and a processor programmed to trigger a new inhalation phase via the control unit 51 when the said filtered difference is higher than a determined threshold.

More precisely, during the expiratory phases, if the volumetric mode is selected, these means 52 constantly monitor the change in the difference between the respective flow rates between the inhalation and expiratory ducts (difference corresponding to the difference in flow rate).

These means 52 are also connected to a memory, and together they can establish during the expiratory phases if the difference in flow rate corresponds:
- if the value of the difference in flow rate remains below a memorized threshold, simply to a leak at the end 120 of the inhalation duct,
- or if the value of the difference in flow rate exceeds this memorized threshold, to a greater difference in flow rate, associated to the start of a demand from the patient for a new inhalation phase—in this case, the means 52 transmit a specific signal to the control unit 51 in order that it adapts the reference values sent to the comparator 151 to trigger a new inhalation phase.

It therefore appears after reading the above description that an apparatus of the invention is advantageous.

In fact, such an apparatus permits the barometric and the volumetric modes to be combined.

It permits control with great precision for wide flow rate ranges.

Furthermore, as we saw above, in volumetric mode, during the expiratory phases it is possible to monitor the difference in flow rate between the inhalation an expiratory circuits and to trigger new inhalation phases automatically, according to the monitoring data.

It may also be remarked that in the case of the invention, the control of the leak rate on the one hand, and the PEP on the other hand, are carried out independently.

It is pointed out that the "leak rate" corresponds to a flow rate that is to be established in the inhalation duct, even during the expiratory phases.

This leak rate corresponds to the flow-by rate.

Such a leak rate is particularly used and known as part of non-invasive ventilation (which is to say that the end 120 of the inhalation duct is in the form of a mask).

The leak rate in the case of the invention is carried out by the inhalation valve 113.

The selective control of the proportional opening of this valve allows the value of the said leak rate to be controlled precisely.

In the apparatus where the inhalation valve is not a specific valve as used in the invention (for example in apparatus where this inhalation valve is a bladder valve similar to the expiratory valve 133), then a leak connection needs to be fitted in parallel to the inhalation valve, to establish a certain pressure in the inhalation circuit 110 even when the inhalation valve is closed.

The use of an inhalation valve capable of proportional operation allows this connection to be dispensed with.

The leak rate is thus controlled by the controlled opening of the inhalation valve, while the PEP is controlled by the microturbine 140 and the expiratory valve.

This disposition is advantageous with respect to apparatus of the existing technique with an inhalation valve of the same type as the expiratory valve 133 of the examples described above.

In the case of these known apparatus when a new inhalation phase is started, the pressure source controls the opening of the inhalation valve pneumatically, which then changes suddenly from a closed position to an open position.

This pneumatic control is provided by a pneumatic connection established directly between the pressure source and the expiratory valve (a similar connection to the 1331 connection shown in these figures that controls the expiratory valve).

The inhalation valve consequently acts like an "all or nothing" valve.

Temporary excess pressure may result in the inhalation duct, which is a source of discomfort for the patient.

This can be especially the case if the pressure source is a turbine, and if a PEP is to be used during the expiratory phases.

In fact this case, given that the value of the PEP depends on the speed of rotation of the turbine, then a suitable reference value must be provided for the speed of rotation (the reference value provided by the connection of the control unit to the pressurized gas source is then typically a speed of rotation reference value).

The speed of rotation of the turbine is then adapted to maintain a PEP of the desired value, by means of a leak connection.

However, when a new inhalation phase is started, this speed of rotation may cause excess pressure in the inhalation duct that is freed by the open inhalation valve.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A breathing assistance apparatus capable of operating in alternating inhalation and expiratory phases, the apparatus comprising:
    a pressurized respiratory gas source,
    an inhalation duct to supply gas from the pressurized respiratory gas source to a patient,
    an expiratory duct for expiratory gas of the patient,
    a set of flow rate sensors positioned to sense a first flow rate of the expiratory duct and a second flow rate of the inhalation duct, and
    a controller, including a processor, configured to control the gas source, the controller further configured to compare the first flow rate and the second flow rate in a volumetric mode, and to trigger a new inhalation phase based on a difference between the first flow rate and the second flow rate,
    wherein the inhalation duct includes an inhalation valve comprising a valve body having an orifice configured to connect to the inhalation duct, and a moving element defining a recess for allowing passage of a gas therethrough, the moving element being translatable relative to the valve body in a first direction such that the orifice and recess are capable of alignment to allow the gas from the gas source to pass through to the inhalation duct in use, wherein a translation of the moving element is proportional to passage of the gas from the gas source through the inhalation duct via the orifice during use.

2. The breathing assistance apparatus of claim 1 wherein the processor is configured to trigger the new inhalation phase based on a determined difference between the first flow rate and the second flow rate.

3. The breathing assistance apparatus of claim 2 wherein the processor is configured to trigger the new inhalation phase based on a comparison of the determined difference and a memorized threshold.

4. The breathing assistance apparatus of claim 3 wherein the processor is configured to trigger the new inhalation phase when the determined difference exceeds the memorized threshold.

5. The breathing assistance apparatus of claim 3 wherein the expiratory duct includes an exhalation valve.

6. The breathing assistance apparatus of claim 5 wherein the exhalation valve is selectively controlled by the controller to move between an open position and a closed position.

7. The breathing assistance apparatus of claim 5 wherein the controller is configured to set the exhalation valve to a closed position in response to the trigger of the new inhalation phase.

8. The breathing assistance apparatus of claim 1 wherein the inhalation valve is selectively controlled by the controller to move between an open position and a proportional position.

9. The breathing assistance apparatus of claim 1 wherein the controller is configured to set the inhalation valve to an open position from a closed position in response to the trigger of the new inhalation phase.

10. The breathing assistance apparatus of claim 1 wherein the expiratory duct includes an exhalation valve, and wherein the controller is configured, in response to the trigger of the new inhalation phase, to set the inhalation valve to an open position from a closed position and to set the exhalation valve to a closed position.

11. The breathing assistance apparatus according to claim 1 wherein the moving element is operable to block the orifice in a closed position, and to at least partially free the orifice in an open position, the recess comprising at least a first part having a geometry corresponding to a proportional operation of the inhalation valve when the first part is aligned with the orifice.

12. The breathing assistance apparatus according to claim 11, wherein the recess is shaped so that when the moving element moves the inhalation valve from the closed position to the open position, the first part is aligned with the recess which causes a progressive opening of the inhalation valve.

13. The breathing assistance apparatus according to claim 12, wherein the first part of the recess is generally triangular.

14. The breathing assistance apparatus according to claim 13, wherein the moving element is designed so that the first part corresponds to angular positions used for volumetric modes.

15. The breathing assistance apparatus according to claim 11, wherein the recess further comprises a second part having a geometry corresponding to all or nothing operation of the inhalation valve when the second part is aligned with the orifice and the second part is aligned with the recess after the first part has aligned with the orifice.

16. The breathing assistance apparatus according to claim 15, wherein the second part of the recess is generally rectangular and the second part corresponds to angular positions used for barometric modes.

17. The breathing assistance apparatus according to claim 1, wherein the moving element includes a variable width, the passage of gas being greatest at a largest width of the moving element.

18. A control method of a controller of a breathing assistance apparatus capable of operating in alternating inhalation and expiratory phases, the method comprising:
    controlling with a controller, including a processor, a pressurized respiratory gas source, the gas source being coupled with an inhalation duct to supply gas from the pressurized respiratory gas source to a patient and an expiratory duct for expiratory gas of the patient,
    with the controller, comparing a first flow rate and a second flow rate, and
    in a volumetric mode, controlling a trigger of a new inhalation phase based on a difference between the first flow rate and the second flow rate,
    wherein the inhalation duct includes a proportional inhalation valve comprising a valve body having an orifice configured to connect to the inhalation duct, and a moving element defining a recess therethrough, and being configured to move laterally with respect to the valve body, a displacement of the moving element being proportional to passage of gas from the gas source through the inhalation duct via the orifice during use, and in response to the trigger of the new inhalation phase, setting the inhalation valve to move to a specific position to allow a desired level of flow through the inhalation valve for delivery to the patient.

19. The control method of claim 18 wherein the trigger of the new inhalation phase is based on determining a difference between the first flow rate and the second flow rate.

20. The control method of claim 19 wherein the trigger of the new inhalation phase is based on comparing the determined difference and a memorized threshold.

21. The control method of claim 20 wherein the trigger of the new inhalation phase comprises determining when the determined difference exceeds the memorized threshold.

22. The control method of claim 20 further comprising controlling an exhalation valve of the expiratory duct.

23. The control method of claim 22 further comprising with the controller, selectively setting the exhalation valve to move between an open position and a closed position.

24. The control method of claim 22 further comprising in response to the trigger of the new inhalation phase, setting the exhalation valve to a closed position.

25. The control method of claim 18 further comprising with the controller, selectively setting the inhalation valve to move between an open position and a proportional position.

26. The control method of claim 18 further comprising in response to the trigger of the new inhalation phase, setting the inhalation valve to an open position from a closed position.

27. The control method of claim 18 wherein the expiratory duct includes an exhalation valve, and further comprising in response to the trigger of the new inhalation phase, setting the inhalation valve to an open position from a closed position and setting the exhalation valve to a closed position.

* * * * *